(12) United States Patent
Kelly et al.

(10) Patent No.: US 6,690,182 B2
(45) Date of Patent: Feb. 10, 2004

(54) EMBEDDABLE CORROSION MONITORING-INSTRUMENT FOR STEEL REINFORCED STRUCTURES

(75) Inventors: Robert G. Kelly, Charlottesville, VA (US); Robert A. Ross, Charlottesville, VA (US); Josef K. Hudson, Charlottesville, VA (US); Stephen H. Jones, Afton, VA (US)

(73) Assignee: Virginia Technologies, Inc, Charlottesville, VA (US)

( * ) Notice: Subject to any disclaimer, the term of this patent is extended or adjusted under 35 U.S.C. 154(b) by 0 days.

(21) Appl. No.: 09/899,908

(22) Filed: Jul. 6, 2001

(65) Prior Publication Data

US 2002/0057097 A1 May 16, 2002

Related U.S. Application Data

(60) Provisional application No. 60/219,370, filed on Jul. 19, 2000.

(51) Int. Cl.[7] .............................................. G01R 27/08
(52) U.S. Cl. ...................................................... 324/700
(58) Field of Search ................................ 324/700, 699, 324/693, 71.2; 205/775.5; 702/34, 35

(56) References Cited

U.S. PATENT DOCUMENTS 6,047,094 A * 4/2000 Kalamkarov et al. ......... 385/12

FOREIGN PATENT DOCUMENTS

WO    2002/06764    * 1/2002

OTHER PUBLICATIONS

Embedded Sensor for Corrosion Measurement, SPIE vol. 3587–0277–786X/99, R. G. Kelly, J. Yuan, S. H. Jones, W. Wang, K. Hudson, A. Sime, O. Schnieder, G.G. Clemena., Mar. 1999.

Embeddable Microinstruments for Corrosion Monitoring, R. G. Kelly, J. Yuan, S. H. Jones, W. Blanke, J. H. Aylor, W. Wang, A. P. Batson, Paper 97294, Nov. 20, 1998.

An ASIC for Electrochemical Measurement of Corrosiivity in Concrete, J. Yuan, W. Wang, S. H. Jones, A. Wintenburg, R. G. Kelly, 1998.

Corrosion Monitoring in Concrete by Embeddable Microinstruments, R. G. Kelly, S. H. Jones, J. H. Aylor, W Wang, A. B. Batson, A. Wintenberg, G. G. Clemena, Jul. 1997.

* cited by examiner

Primary Examiner—Michael Nghiem
(74) Attorney, Agent, or Firm—Sheldon H. Parker

(57) ABSTRACT

A system for monitoring the material changes in a structure is disclosed through the use monitoring instruments embedded within the structure. The instruments have at least one sensor with electrodes in contact with the surrounding material and electronics that are contained within the instrument. The sensor signals are converted to digital and transmitted to an external data logger or computer for display of the digitized signals. The connection between the microcontroller and the data logger can be either through hardwire or RF. Power is provided to the electronic sensors through either external or local methods. A power management system can be used to place the electronics into a sleep mode when not in use. The electronics are encapsulated within potting material within an instrument case that is manufactured from a material having a flexural modulus equal to, or greater than, the surrounding material to prevent mechanical failure of the device before failure of the surrounding material. The case has protective trays to protect the electrodes and rounded adjacent connection lengths to prevent the case from developing cracks.

24 Claims, 11 Drawing Sheets

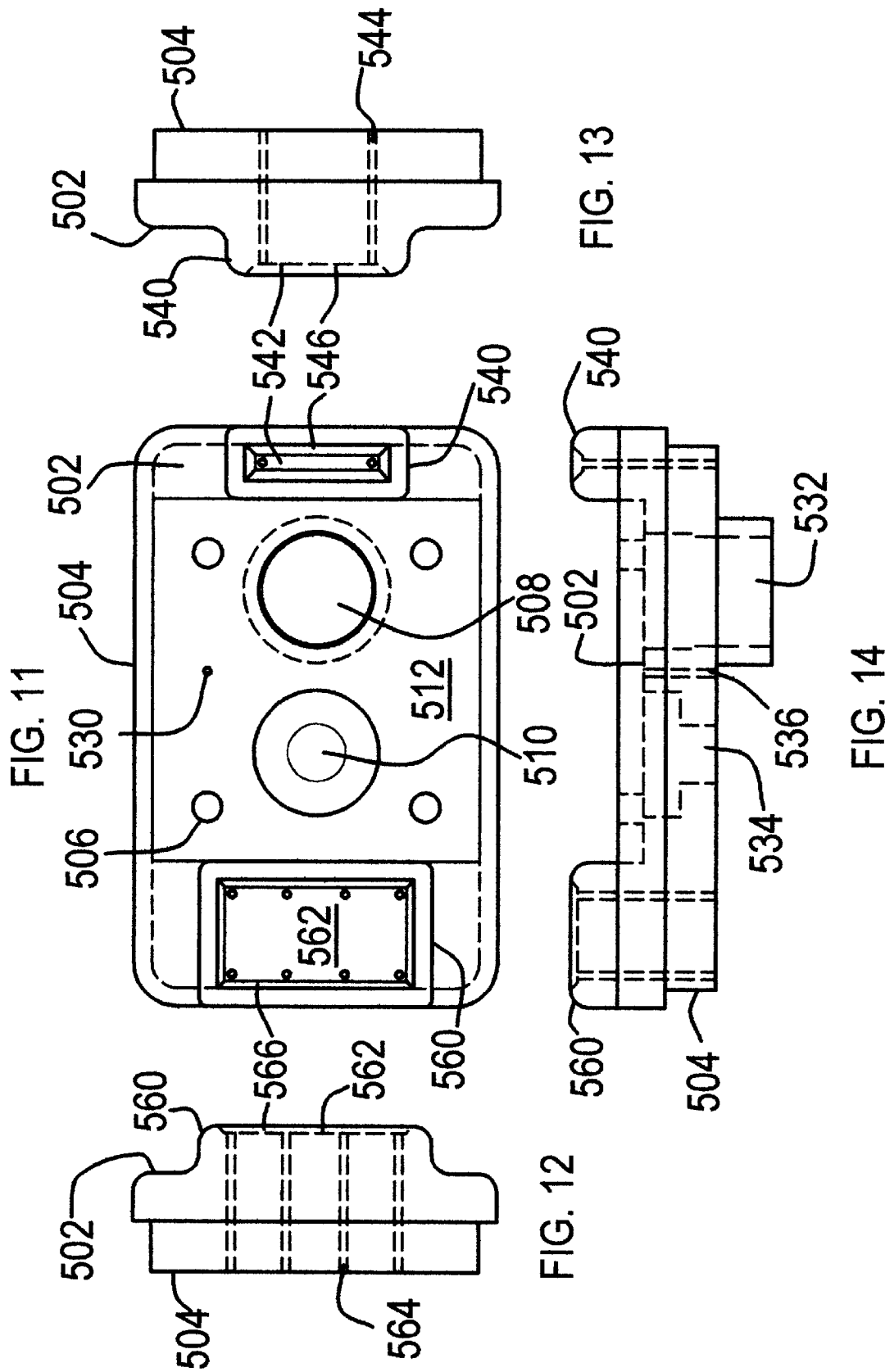

EMBEDDABLE CORROSION MONITORING-INSTRUMENT FOR STEEL REINFORCED STRUCTURES

CROSS-REFERENCE TO RELATED PATENT APPLICATION

The present application claims the benefits under 35 U.S.C. 119(e) of provisional patent application Ser. No. 60/219,370, filed Jul. 19, 2000. This application incorporates by reference, as though recited in full, the disclosure of co-pending provisional application 60/219,370.

BACKGROUND OF THE INVENTION

1. Field of the Invention

The invention relates to a device to monitor corrosion and other structural changes in steel reinforced structures, such as concrete bridges, roadways and load bearing support members. This instrument is fully embeddable and becomes a permanent component of the structure.

2. Brief Description of the Prior Art

Corrosion monitoring has been a recognized problem and has been addressed by the prior art. Unfortunately, the prior art has a number of weak points that render the more exacting readings impossible. Further, the prior art technologies have concentrated on instruments which are specifically designed to be embedded in steel reinforced concrete structures and monitor electrochemical corrosion related parameters and cannot be used for other applications.

The use of Ag/AgCl reference electrodes present a long-term stability issue that is overcome in the disclosed device through the use of MnO2 reference electrodes, thereby enabling the instrument to produce accurate and repeatable measurements over its useful lifetime.

The prior art corrosion monitoring devices embedded the electrode containing probe in the concrete with a cable connecting the electrode to the electronic instrumentation and power source at the exterior of the structure. Although this makes the electronic instrumentation and power source accessible, this system adversely affects the accuracy of the readings by making the accuracy inversely proportional to the length of the cable between the electrodes and the analog signal processing electronics.

This inaccuracy problem was overcome in the disclosed system through the inclusion of the electronic sensors within the instruments. By placing the electronic sensors within the instruments, the signal loss is dramatically reduced, enabling far more accurate readings.

The use of integrating type A/D converter integrated circuits with 16-bit resolution within the prior art devices has also created accuracy problems. The accuracy of an integrating type A/D converter is largely dependant upon the performance of external components such as the converter system's integrating capacitor. The capacitance value of external integrating capacitors can vary significantly with changes in ambient humidity and temperature, making them sub-optimal for embedded instrument applications in any material that is subject to being affected by ambient changes. Also, these converters do not have the ability to perform on-chip amplification and filtering which is important when processing analog signals having a low signal to noise ratio. The disclosed device has overcome this problem through the use of a high-resolution 24-bit sigma/delta type A/D converter with programmable gain amplifier and low pass filter.

An additional problem encountered by prior art devices are that they are only capable of communication with one other device and are not capable of networked multi-point communications. They further do not have the capability to keep track of time or have on-board data-logging capability. The disclosed devices are capable of digital communication with one another as well as with a single external data collection instrument. The networking, in combination with the "real time clock" enables controlled scheduling of tests, reporting of data, etc.

The need to improve the methods of monitoring structural materials has been recognized. In 1998–1999 research was done and articles published regarding the advantages of measuring corrosion electrochemically. *Embedded Sensor for Corrosion Measurement,* SPIE Vol. 3587-0277-786X/99, R. G. Kelly, J. Yuan, S. H. Jones, W. Wang, K. Hudson, A. Sime, O. Schneider, G. G. Clemena;

One method of solving the problem of embedded electrodes was to place everything on a chip using on chip or off chip electrodes. The problem with this method is that when on chip electrodes are used, there is insufficient surface to provide accurate readings. The incorporation of outboard electrodes present the same problem as prior art devices with an inability to transmit a strong enough signal over the distance between the electrode and the electronics. This technology only used a potentiostat having a simple signal in/signal out capability. *Embeddable Microinstruments for Corrosion Monitoring,* R. G. Kelly, J. Yuan, S. H. Jones, W. Blanke, J. H. Aylor, W. Wang, A. P. Batson, Paper 97294, 1997.

In *An ASIC for Electrochemical Measurement of Corrosivity in Concrete,* J. Yuan, W. Wang, S. H. Jones, A. Wintenberg, R. G. Kelly uses a chip with a potentiostat and a galvanostat that rely on off board electrodes and separate processor. This again continues the prior art problem of losing signal due to the transmission distance. The *Corrosion Monitoring in Concrete by Embeddable Microinstruments;* R. G. Kelly, J. Yuan, S. H. Jones, J. H. Aylor, W. Wang, A. B. Batson, A. Wintenberg, G. G. Clemena again uses an arrangement similar to that of the foregoing monitoring instrument, without overcoming the loss of signal problem. *Embeddable Microinstruments for Corrosivity Monitoring in Concrete,* R. G. Kelly, S. H. Jones, O. M. Schneider, W. Wei, J. Yuan, A. Sime illustrates a Power Point presentation of the technology using the ASIC and, obviously continues to have the same limitations as the original presentation.

The prior art trend was toward extreme miniaturization through the design of an ASIC (application specific integrated circuit). This miniaturization presented the problem that the circuits performance wasn't sufficiently high to monitor and transmit repeatable and accurate signals. Additionally, the expense involved in the design and development of an ASIC is so high that the addition of varied, or multiple monitoring, brings the costs above practicality.

In addition to the resolution of the loss of signal, none of the articles address the environmentally specific issues associated with protecting the embedded electronics and electrodes from mechanical damage in a potentially rugged material. Nor was the issue of how to accurately read one or more instruments addressed. The prior art did not, however, address the networking and data sharing issues that are required for the accurate coverage of large structures such as bridges, multi-story buildings, etc. Not only is the networking and data sharing of instruments far more complicated than connecting two instruments via a point-to-point connection, the signal must be accurately transmittable.

These and other problems have been overcome by the disclosed invention to produce an embeddable monitoring device where the electrodes, sensor electronics and microprocessor are all contained in a ruggedized and moisture tight case. The proximity of the electrodes, sensor electronics and microprocessor enables the transmission of maximum signal, more accurate readings and networkability.

SUMMARY OF THE INVENTION

A system for monitoring the material changes in a structure is disclosed through the use of at least one monitoring instrument embedded within the structure. For large structures, the instruments can be networked to provide readings from each specific portion of the structure. The monitoring instruments have at least one sensor with each sensor having electrodes in contact with the surrounding material. Electronics for each electrode are contained within the instrument and receive analog signals from the electrodes. An analog to digital converter converts the signals from each of the sensor prior to the signals being sent to a microcontroller. The analog to digital converter also amplifies and filters the signals and, in one embodiment, the amplification and filtration are programmable from the data logger. A digital to analog converter converts signals being sent to the electronic sensors from the microcontroller. A transmission device transmits the digital signals from the microcontroller to an external data logger or computer for display of the digitized signals. The connection between the microcontroller and the data logger can be either through hardwire or radio frequency (RF). A real time clock, in two-way communication with the microcontroller, can also be incorporated. Power is provided to the electronic sensors through either external or local methods. To conserve power, a power management system can be used that is in communication with each of the electronics sensors, the analog to digital converter, microcontroller, and digital to analog converter. The power management system regulates the power consumption by placing any of the electronic sensors, analog to digital converter, microcontroller, and digital to analog converter into a sleep mode when not in use.

When the system is used to monitor corrosion a galvanostat, or equivalent, is used to measure conductivity and a potentiostat or its equivalent used to measure linear polarization resistance. Chloride concentration is measured through the use of an Ag/AgCl electrode that is Cl⁻ ion specific, and a MnO2 reference electrode by measuring the voltage potential between the ion specific electrode and the MnO2. The device can alternatively use a steel working electrode and a stainless steel reference electrode to measure the linear polarization of the area surrounding the instrument by matching the exterior surface of the steel working electrode to the exterior surface of the surrounding support steel.

When using local at least one of a piezoelectric generator; an electrochemical galvanic couple; and/or a RF power receiver using an impedance matching network is used. Preferably a combination of the piezoelectric generator, electrochemical galvanic couple and RF power receiver are used and serve as an alternate power source to one another.

To protect the electronic sensors and enable them to be embedded into the structural material an instrument case is used that is manufactured from a material having a flexural modulus at least equal to said structural material stress divided to by said structural material strain. The flexural modulus equal to, or greater than, the concrete preventing mechanical failure of the device before failure of the concrete. The instrument case has a hollow body with a removable first end, a closed second end and multiple sides, each of the multiple sides having a connection length with an adjacent side. The body is configured to contain and protect the electronic sensors from contact by with the structural material. The removable first end has at least one electrode receiving port and, in the preferred embodiment, at least one protective tray. The protective trays extending from the face at about a right angle to surround the electrode receiving ports, thereby enabling the electrodes to be raised from the surface of the first end. The instrument has at least one cable port to receive a network cable for connection to other instruments and/or a power source. The adjacent connection lengths are rounded to direct pressure from the surrounding structural material around the instrument case to prevent cracks from forming due to the pressure asserted by the surrounding material. The first end of the instrument case contains receiving ports to receive the external electrodes of the electrical sensors, placing a first end of each electrode in contact with said structural material and a second end each electrode in electronic contact with the electronics within the instrument case. The instrument case preferably has attachment flanges integral to the hollow body with tie receiving channels to enable the instrument case to be attached to the surrounding steel structure. The modules are protected within the instrument case by potting material preferably having sufficient flexibility to permit the enclosure to flex without compressing against the electronic components.

BRIEF DESCRIPTION OF THE DRAWINGS

The advantages of the instant disclosure will become more apparent when read with the specification and the drawings, wherein:

FIG. 11 is a front view of the face of the instrument case, FIG. 12 is a side view of one of the protective trays, FIG. 13 is a side view of a second protective tray;

FIG. 14 is a top view of the cover of the instrument case;

DETAILED DESCRIPTION OF THE INVENTION

Figure 1:
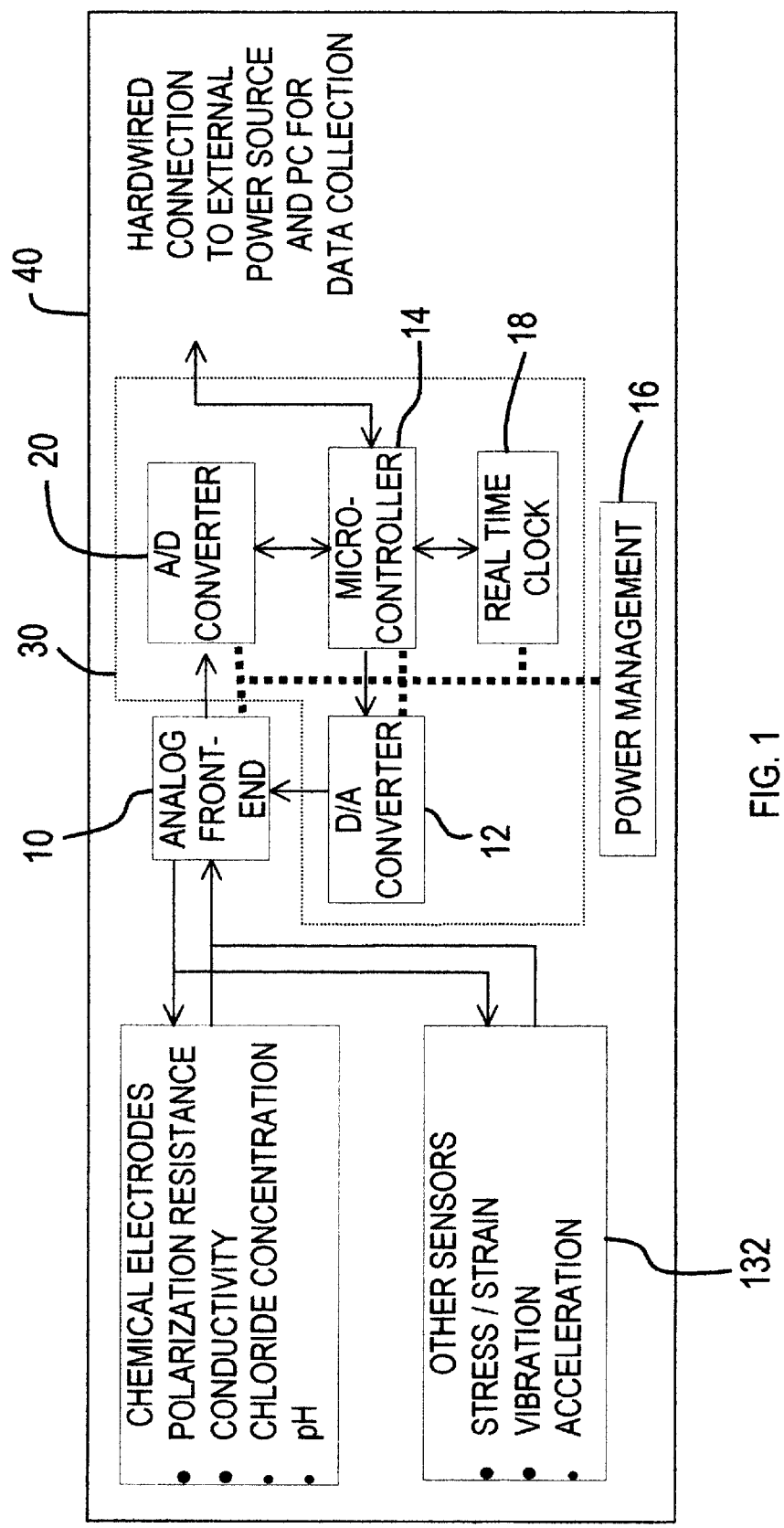
FIG. 1 is a block diagram of the monitoring instrument.

An embeddable corrosion measuring instrument is disclosed that is capable of providing information related to corrosion rate, corrosion potential, conductivity and chloride concentration, pH levels, vibration levels, stress and strain levels and temperature of steel rebar reinforced structures. By monitoring the integrity of the steel, without referencing the surrounding materials, the disclosed device can be used in a greater number of structures than the prior art devices. Many prior art devices require a direct electrical connection to the reinforcement steel within the structure, using the structural steel as one of the referencing materials. Since the disclosed instruments do not require proximity to the steel within the structure, the instruments can be dispersed at critical locations within the structure, regardless of steel placement. This is accomplished through the incorporation of a sacrificial working electrode within the instrument, thereby enabling readings to be taken from the working electrode rather than the structural steel. In order to obtain accurate readings, the working electrode must be the type of rebar, or other metal, being monitored. For example, if the rebar used within a structure is epoxy coated, then working electrode must also be epoxy coated. Additionally, if several types of treated or coated structural reinforcements are being used in a single structure, the monitoring instruments placed proximate each type of reinforcement should contain a matching working electrode. Additionally, since the instrument is self-contained, incorporating all required sensing electrodes and electronics as illustrated in FIG. 1, it can be used in applications unavailable to prior art devices.

It should be noted that other sensors can replace those disclosed herein dependent upon end use. For example, a temperature sensor can be added to enable the curing rate of the concrete to be monitored. The temperature, with the output of the conductivity sensor, provides accurate readings of the internal curing of the structure. Further, the addition of ambient humidity and temperature sensors, permits the microprocessor to calculate what is required for that day for optimal curing. Additionally, the chloride sensor enables the salt and other foreign substance content of the concrete to be monitored, thereby maintaining quality control of the materials being used. By providing monitoring capabilities during building and curing, the disclosed monitors can provide valuable data that ensures quality control at the onset of building the structure, but provides data needed by the microprocessor to predict the life span, faults and/or required repairs of the structure over the life of the structure.

In many prior art devices a probe containing the sensors is placed in the material and a cable run to the externally located electronics used to analyze the signals received from the sensors. As the signals indicative of corrosion are so small, the distance between the probe and the electronics must be severely limited in order to obtain accurate and repeatable measurements. Since the disclosed device contains the electronics within an embedded unit, the distance between the probes and the electronics is minimal. The ability of the disclosed instruments to communicate with the data collection system, as well as each other, via a digital network enables the distance between the disclosed instrument and the power source/data logger and/or read out, to be substantial. The distance between the power source/data logger and the disclosed instrument is dependent upon the network being used, for example an RS485 network permits about 4000 feet. Even greater distances can be obtained through the use of multiple networked instruments, with the number of instruments being only limited by the network structure. In this way, a bridge can have optimal coverage with the only requirement being that the instruments be distanced from one another no more than the maximum distance permitted by the network. Although the description herein is directed to monitoring the corrosion of steel reinforced concrete, it should be noted that this device can be modified to accommodate other corrosive environments, such as chemical parameters as well as physical parameters in a wide range of environments through the selection of appropriate electrodes and/or sensors. The addition of pH, strain, vibration, and acceleration measurement capability substantially broadens the uses of the disclosed instruments. pH is an indicator of the presence of corrosion in many environments and strain gauges are commonly used to monitor the movement of cracks and other defects that develop in structures due to corrosion or other degradation processes (e.g., mechanical damage). Having strain monitoring capability in the instrument allows engineers to monitor the structural defects and make informed repair and condition based preventative maintenance decisions. The capacity to measure the amplitude and frequency of vibration allows engineers to determine when these parameters exceed design specifications for the structure and take preventative action to reduce vibration before structural integrity is compromised. For example, the number of vehicles allowed to cross a bridge at any given time can be limited. Similarly, the capacity to measure acceleration in one to three dimensions in a structure can be used to detect and prevent destructive modes of oscillation. In earthquake prone areas, instruments equipped with this capability can be embedded into bridges, or other roadway structures, and used to detect and warn motorists of seismic activity. The instruments can also be placed into "earthquake proof" buildings to monitor the structural integrity of the building. The instrument can also be used to monitor corrosion in a closed loop, cathodic protection system.

Figure 2A:
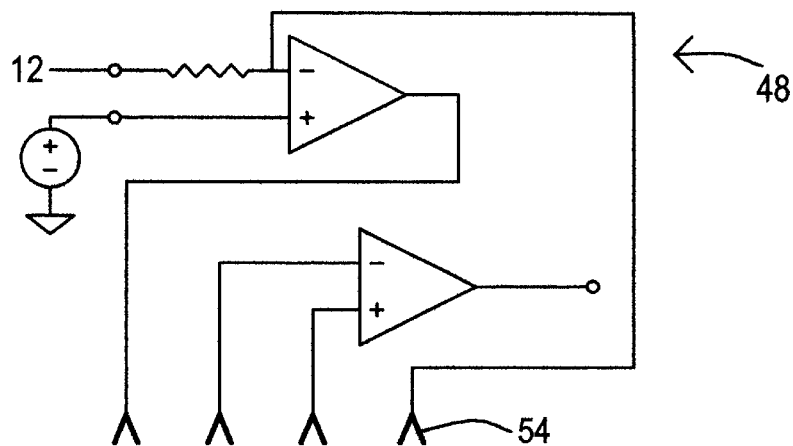
FIG. 2a is a block diagram of an example galvanostat for use with the disclosed monitoring instrument.
Figure 2B:
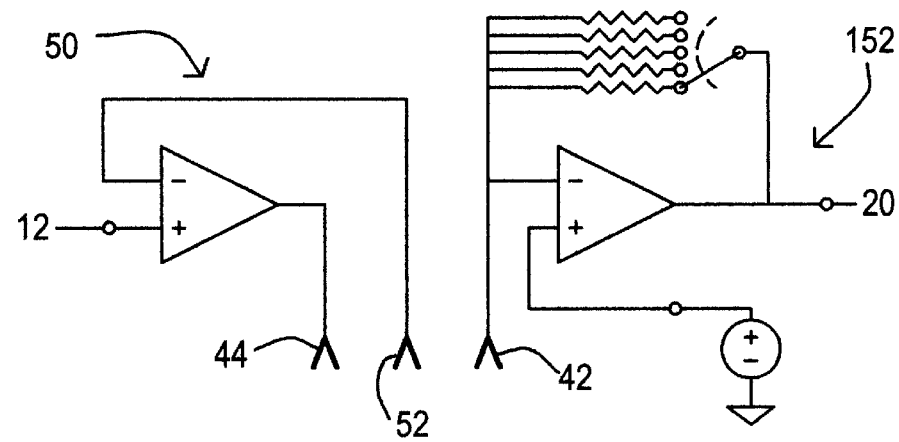
FIG. 2b is a block diagram of an example potentiostat and zero resistance ammeters for use with the disclosed monitoring instrument.
Figure 2C:
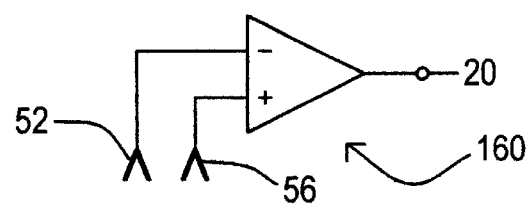
FIG. 2c is a block diagram of example chloride measuring electrodes and circuit for use with the disclosed monitoring instrument.

FIGS. 2a, 2b and 2c illustrate the three electronic sensors, which are in this embodiment corrosion measuring sensors, that are part of the analog front end 10. As seen in FIG. 2a a four-pin or stainless steel conductivity sensor electrode 54 is leading to a galvanostat 48 capable of conductivity/resistivity measurement. In aforenoted research, the conductivity sensor electrode was made from gold. The use of stainless steel not only reduced the cost of the unit, but it provides increased structural integrity. The preferred stainless steel is 316 L austenitic, low carbon. The low carbon is required if the stainless steel is welded as the carbon will affect the life of the electrode. In FIG. 2b the electrodes include a segment of reinforcing steel as a working electrode 42, stainless steel mesh counter electrode 44 and a MnO2 reference electrode 52 leading to a potentiostat 50 capable of linear polarization resistance measurement. In the aforenoted research a platinized niobium was used for the mesh counter electrode, however it has been found that the 316 L stainless steel not only provides cost effectiveness, but increased durability. Alternatively, a stainless steel plate can be use rather than the mesh. The stainless steel is additionally easier to connect to the body of the instrument. The stainless steel used for the conductivity electrodes is preferably about 0.043 of an inch thick rather than the prior art use of 0.021 of an inch, thereby increasing the stability. The heavier gauge further provided additional surface area, which in turn provides more accurate readings due to a higher signal.

In the preferred embodiment all electrodes monitoring a diffusing substance extend an equal distance from the face of the instrument. This ensures that the substance being monitored reaches all electrodes at approximately the same time, thereby enabling more accurate measurements. In the event an electrode monitoring a diffusing substance is not at an equal distance with corresponding electrodes, the software can be programmed to compensate for this differential. In other words, if device is embedded in concrete with the working electrode extending above the face of the device ¼ inch more than the conductivity electrodes, and the corrosion substance migration time period is known, the differential between the data collected from the two electrodes can be calculated. The data received from each electrode can then be correlated at the data logger to provide for a variety of calculations and comparisons to better pinpoint the timeframes of potential weakness within, or failure of, the structure.

FIG. 2c shows an Ag/AgCl electrode 56 and MnO2 reference electrode 52 leading to a circuit 160 capable of measuring a voltage proportional to chloride concentration. The MnO2 reference electrode can be replaced with stainless steel, to provide costs efficiency, and will depend upon the final use. The replacement of the Manganese Dioxide electrode will eliminate the ability to monitor chloride ions, however this measurement is not applicable in all instances and this, and other measurements will be evident to those skilled in the art.

A portion of all electrodes 42, 44, 52, 54 and 56, as well as the internal leads are mounted into a plastic, liquid tight enclosure, such as the instrument cases disclosed hereinafter, containing the instrument's electronics. In order to protect the instruments, a waterproof, nonconductive potting material is used. An example of an appropriate material for many applications is one having a Poisson's ratio of 0.5 or an equivalent. The potting material must provide sufficient flexibility to permit the instruments to flex while not compressing, thereby damaging the electronics. Since the potting material will be subjected to temperature extremes, as well as in many instances long periods of vibration, there will be a fine ratio between the flexibility and stiffness. The appropriate material used in each application will be evident to those skilled in the art when read in conjunction with the criteria taught herein.

Figure 3:
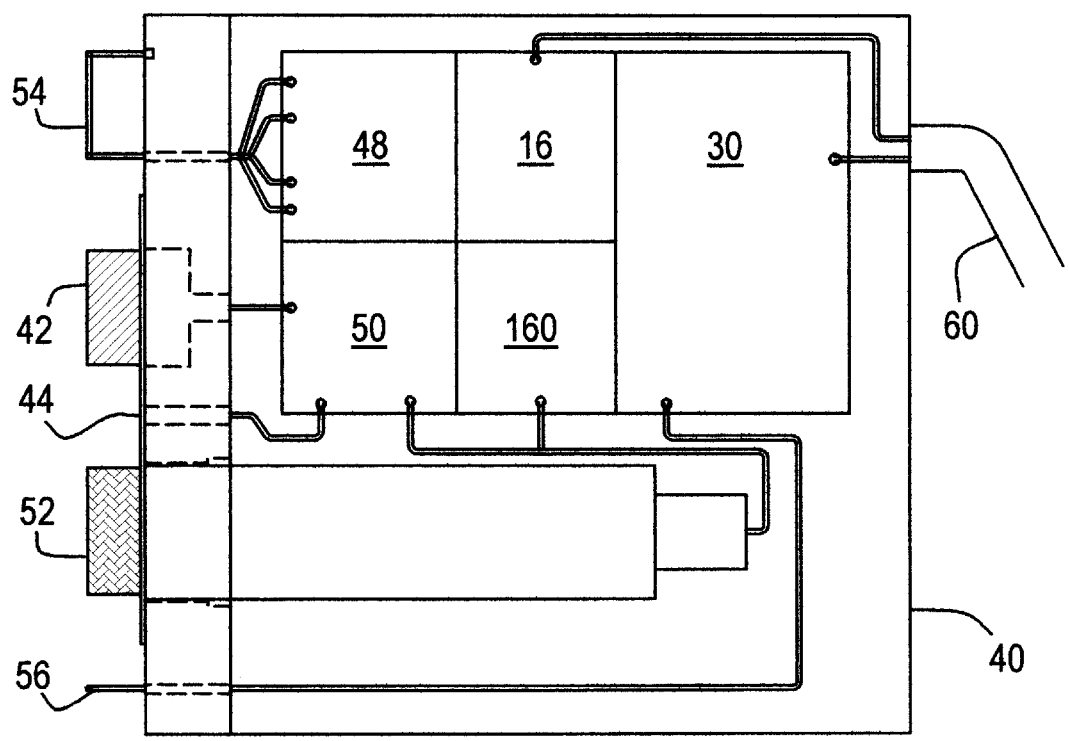
FIG. 3 is a cutaway top view of the disclosed monitoring instrument.

As shown in FIG. 3, a portion of the electrodes of each of the electronic sensors generally extend beyond the monitoring unit 40 to obtain the readings from the surrounding material. Whether the electrodes extend from the monitoring unit and how much of an extension is required is dependent upon the type of sensor being used and the material being monitored. The electrodes monitor the shifts in material, whether it is chemical, seismic, temperature, etc., and transfer these shifts to the appropriate internal electronic sensors, such as the illustrated potentiostat 50, galvanostat 48, and chloride sensor 160. This architecture is also applicable for any additional sensors 132 which may be required for a specific application. All of the electronic sensors send the data directly to the instrument control module 30, which contains the microcontroller 14, A/D converter 20, D/A converter 12 and real time clock 18. Since the distance between the exposed portion of the electrode and the internal electronic sensors is minimal, the shifts read by the electrodes are not lost or distorted within the connections between the electrode and the electronic sensors. Each of the electronic sensors is directly linked to the instrument control module 30. Within the control module 30, the readings are converted from analog to digital at the converter 20 and sent to the microcontroller 14 where they are transmitted, through appropriate transmission means using either a hardwire connection or RF, to the receiving computer or other data logger. As used herein RF includes, but not limited to, inductively or capacitively coupled radio frequency identification (RFID) technology, for example as RF tag or Bistatix™. Although a computer provides the advantage of additional calculations or transmission of the sensor readings, in some applications a display panel can be sufficient.

The sigma-delta type A/D converter system, or its equivalent, used herein provides superior performance as compared to integrating type A/D converters. For optimum results, the converter system should provide 24-bit resolution, contain on-chip resources for signal amplification and filtering and use external components that are highly resistant to changes in humidity and temperature. These features allow this type of converter system to be most appropriate for use in embedded instrument applications. The sigma-delta type A/D converter system significantly increases the accuracy of the measurement results as compared to previously disclosed devices.

Figure 4:
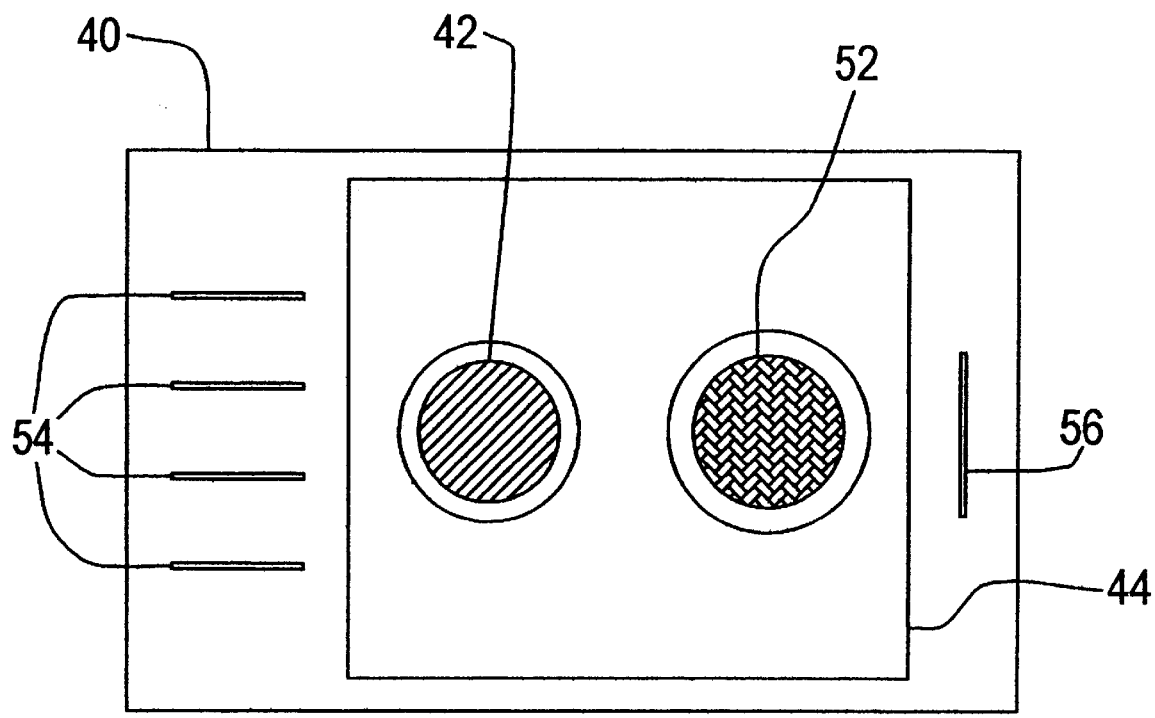
FIG. 4 is a front view of the disclosed monitoring instrument.

As shown in FIG. 4, the mesh counter electrode 44 covers a major portion of the face of the monitoring device. The potentiostat 50 requires the use of a working electrode 42, counter electrode 44 and reference electrode 52. An electric field is present between the counter and working electrodes 44 and 42 during a measurement cycle. The reference electrode 52 must be placed such that it is in that field. Therefore, the counter electrode 44 must have sufficient surface area to surround both the working and reference electrodes 44 and 42, while not coming in contact with the Ag/AgCl electrode 56 or the conductivity electrodes 54, as these are not part of the potentiostat 50.

Figure 5:
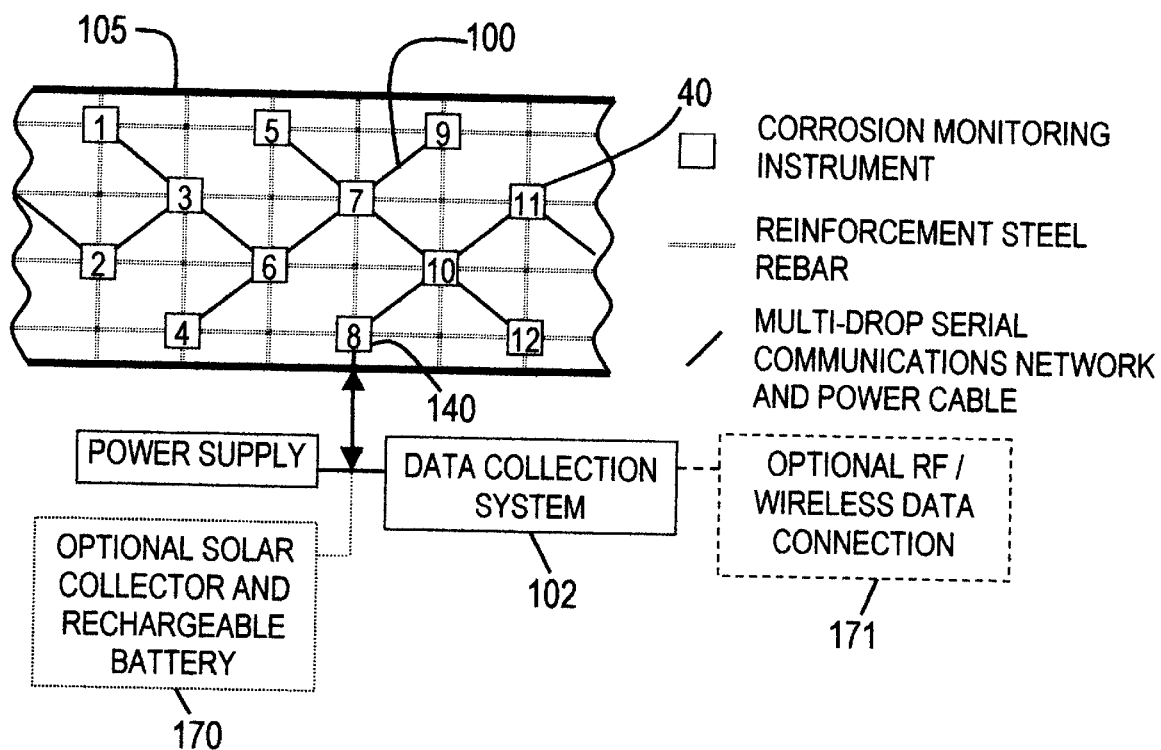
FIG. 5 is a top view of hardwired network of instruments embedded in a bridge or roadbed structure.

As seen in FIG. 5, a number of instruments 40 can be interconnected, through communication and power cables 100 to form a hardwired embedded digital local area network (LAN). The network enables each instrument to communicate with other embedded instruments within a structure, as well as with an external data collection system. Physical layer implementations of this network include RS-232, RS-485, TTL, CMOS, 4–20 mA current loop, or high speed low power low voltage differential signal (LVDS). The embedded instruments can communicate using a range of industry standard protocols including SDI-12, HART, CAN and LON Works. Because of this LAN capability, a number of useful functions can be implemented which were not possible in prior art devices, Each of the instruments 40 is programmed with a unique ID code, thereby enabling each instrument 40 to send and receive specifically addressed communications. A sufficient number of instruments 40 are placed in known locations, with ID's and locations noted throughout the structure 105 in order to provide an accurate map of corrosion, stress, temperature and vibrational parameters. In this configuration, each uniquely addressable instrument 40 can communicate with the external data collection system 102. In the preferred embodiment, this communication is bidirectional to enable the external data collection system 102 to issue commands to a specific, uniquely addressed, instrument 40 and that instrument 40 can provide the appropriate response. These commands can include, for example, an instruction for the instrument 40 to begin a measurement; with the instrument 40 subsequently responding with the appropriate data after the measurement is complete. The collections system 102 could also command an instrument to schedule single or multiple measurements at a later time. As each of the instruments 40 preferably has an internal data logging capability, it is able to store the results of a number of prescheduled measurement cycles. The external data collection system 102 can either issue a command for each instrument to download its logged and time-stamped measurement results or include a download time in the original command. In the hardwired configuration, power is also supplied to each instrument through the hardwired connection 100. Optimally, each of the instruments 40 can communicate bi-directionally with one another as well as with the collections system 102. This enables the instruments to perform such tasks as calibrating time, instrument tests, etc. A notification can be sent to the collection system 102 in the event of inaccurate calibrations. Additionally a "lead" unit 140 can be assigned with the task issuing commands and collecting data to and from other instruments 40 on the network. Once the lead unit 140 has been programmed, these commands would be issued at specific time intervals requiring no intervention from the user. The data collection system 102 can interface with an optional RF/wireless data connection 171 for the remote retrieval of data and reprogramming of the instruments 40 via the data collection system 102. This RF/wireless data connection could include a variety of technologies such as RF, terrestrial cellular and satellite communications. Optionally this configuration can be powered by a rechargeable battery, which is charged by a solar collector 170.

Figure 6:
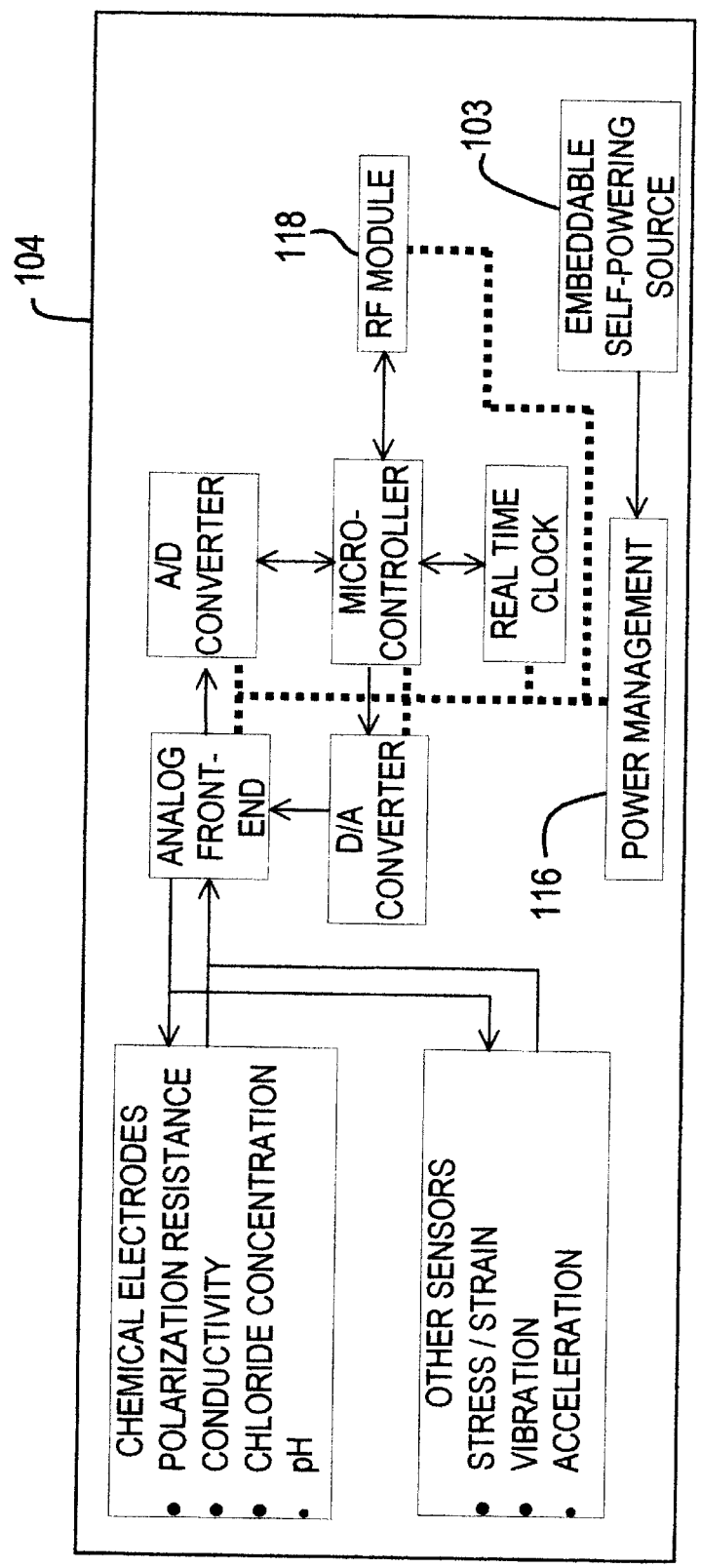
FIG. 6 is a block diagram of the wireless corrosion measuring instrument.
Figure 7:
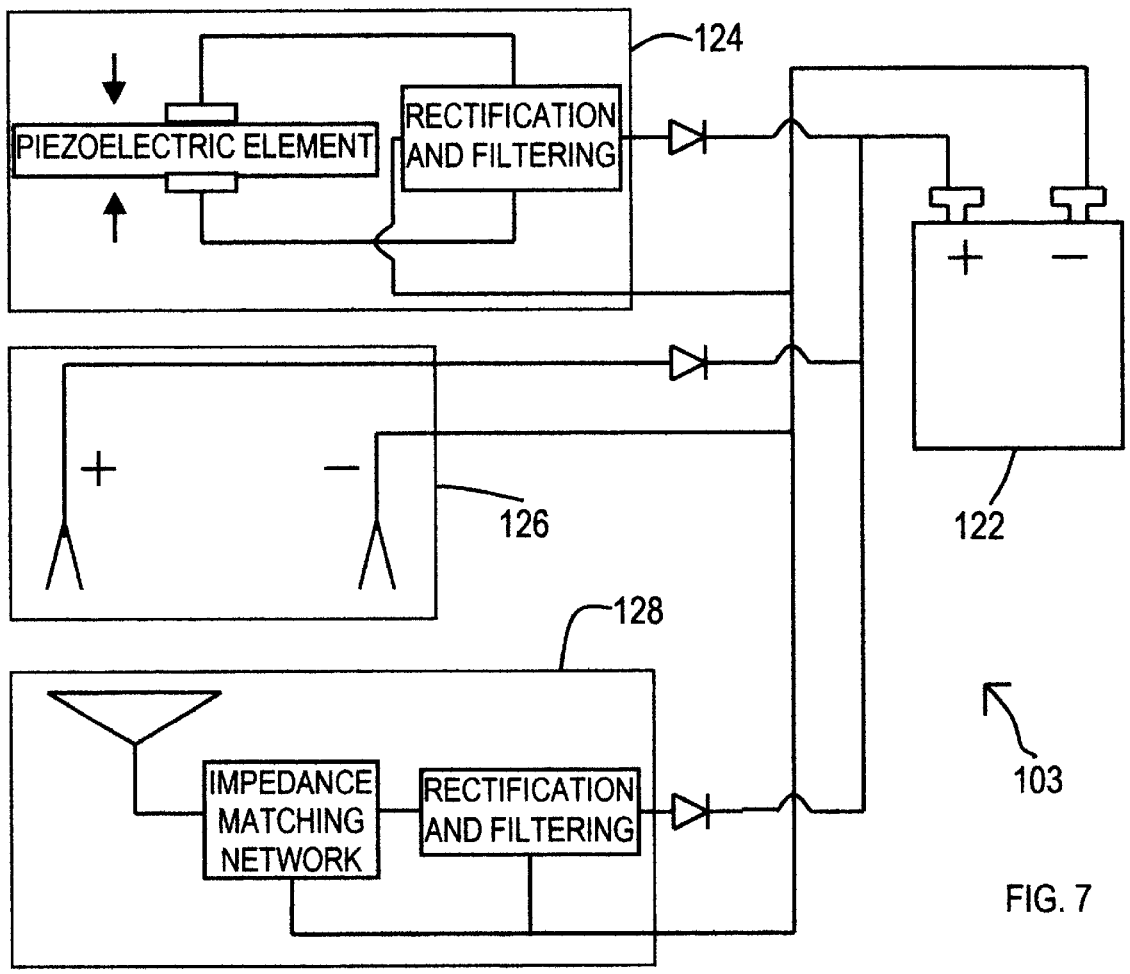
FIG. 7 is a block diagram of the embeddable self-powering unit.

In the wireless configuration, each embedded instrument 104 shown in FIG. 6 contains an RF communications module 118, a power management system 116 and is powered by an embeddable self-powering source 103, a detailed example of which is shown in FIG. 7. The powering source 103 consists of an energy storage device 122, such as a rechargeable battery or a high capacity "super capacitor" type device. The energy storage device is charged using a piezoelectric generation device 124, or equivalent generator, a series of electrochemical galvanic couples 126, and an RF power receiver 128, or any combination thereof. Although a single charging device can be used it is preferable to have a combination of at least two, and preferably three, devices. This configuration allows one or more charging devices to charge the energy storage device 122 at any given time. For example, all three units can be operational simultaneously; if the structure is vibrating, activating the piezoelectric generation device 124; the chemistry within the structure is such that the galvanic couples 126 can produce energy; and the instrument is receiving RF energy from external RF source processed by the instrument's power receiver 128. The RF energy applied from outside the structure under inspection as well as energy derived from the piezoelectric generation device 124 can be rectified, filtered and converted to a DC potential.

Figure 8:
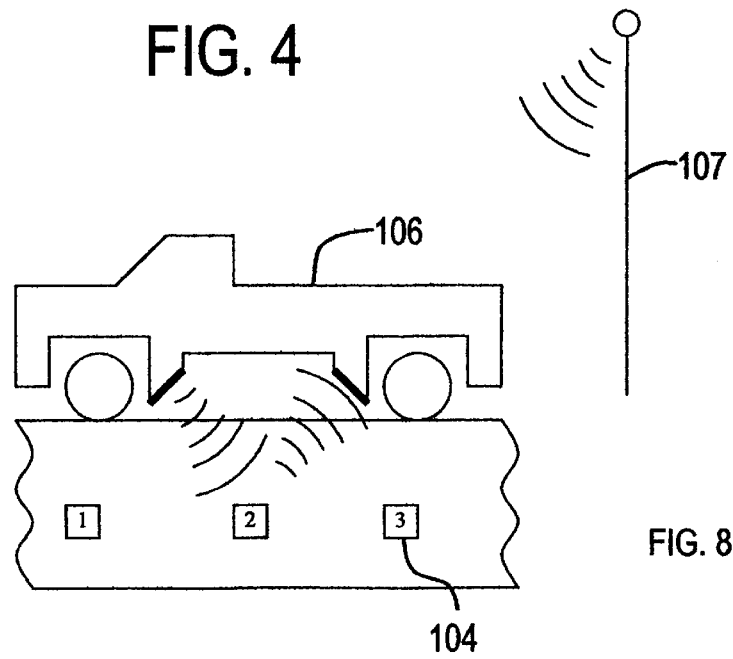
FIG. 8 is an example of a wireless network of instruments embedded in a bridge or roadbed structure.

In this embodiment, an RF sensor can be attached to, or included within, the wireless monitoring instrument 104 allowing it to communicate via a wireless connection as shown in FIG. 8. In the wireless network configuration, the data collection system 106 is located in a vehicle or other portable device. The data collection system 106 is passed along the external surface of the structure in which the instruments 104 are embedded. Each of the embedded corrosion monitoring instruments 104 and the external data collection system 106 includes a bi-directional radio frequency (RF) transceiver. In the illustrated RF system the data collection system is a truck carrying an RF transceiver. Alternative methods of activating and collecting data may include a stationary RF transceiver 107 nearby the structure in which instruments 104 are embedded. Other such data collection systems are possible and will be evident to those skilled in the art. As an alternative to using an RF transceiver, each embedded instrument can communicate with the external data collection system using RF tag or Bistatix™ technology. These technologies are highly energy efficient since they typically do not require a DC power source to operate. RF or inductively or capacitively coupled RFID" devices communicate with compatible reader devices by passively modulating the incoming RF energy produced by the external reader device itself. Similar in operation to the hardwired network previously described, the data collection network can communicate with each uniquely addressable instrument.

Preferably the monitoring instruments use commercial off the shelf electronic components, however in some applications customized materials can be required. As the goal was to achieve a maximum dimension of less than 3.5"×2.5"× 2.5", surface mount technology is used extensively. In applications where size is not a determining factor, the materials used, the method of encasement and mounting will have more flexibility and the overall device will be easier to manufacture. For ease of description, the optimal embodiment will be described.

Analog Front-end Electronics

The instrument 40's analog front-end 10, the circuits of which are illustrated in FIG. 2, is responsible for amplification of the low level signals collected from the instrument's sensing electrodes. It is also responsible for producing excitation potentials to drive these electrodes. Several important corrosion monitoring parameters ($E_{corr}$, $I_{corr}$, conductivity and [$Cl^-$]) use very similar circuitry involving operational amplifiers and instrumentation amplifiers as basic building blocks. These amplifiers have extremely high input impedance and are capable of measuring voltages without affecting the potentials being measured. Measurements of $E_{corr}$ and [$Cl^-$] require such buffered measurement due to the desire to limit currents flowing through these circuits to extremely low values in order to avoid affecting the environment under study. The $E_{corr}$ measurement compares the voltage of the steel working electrode 42 to that of a reference electrode 52. A voltage proportional to [$Cl^-$] can be quantitatively measured by monitoring the potential between an Ag/AgCl ion specific electrode 56 and the MnO2 reference electrode 52.

Figure 10:
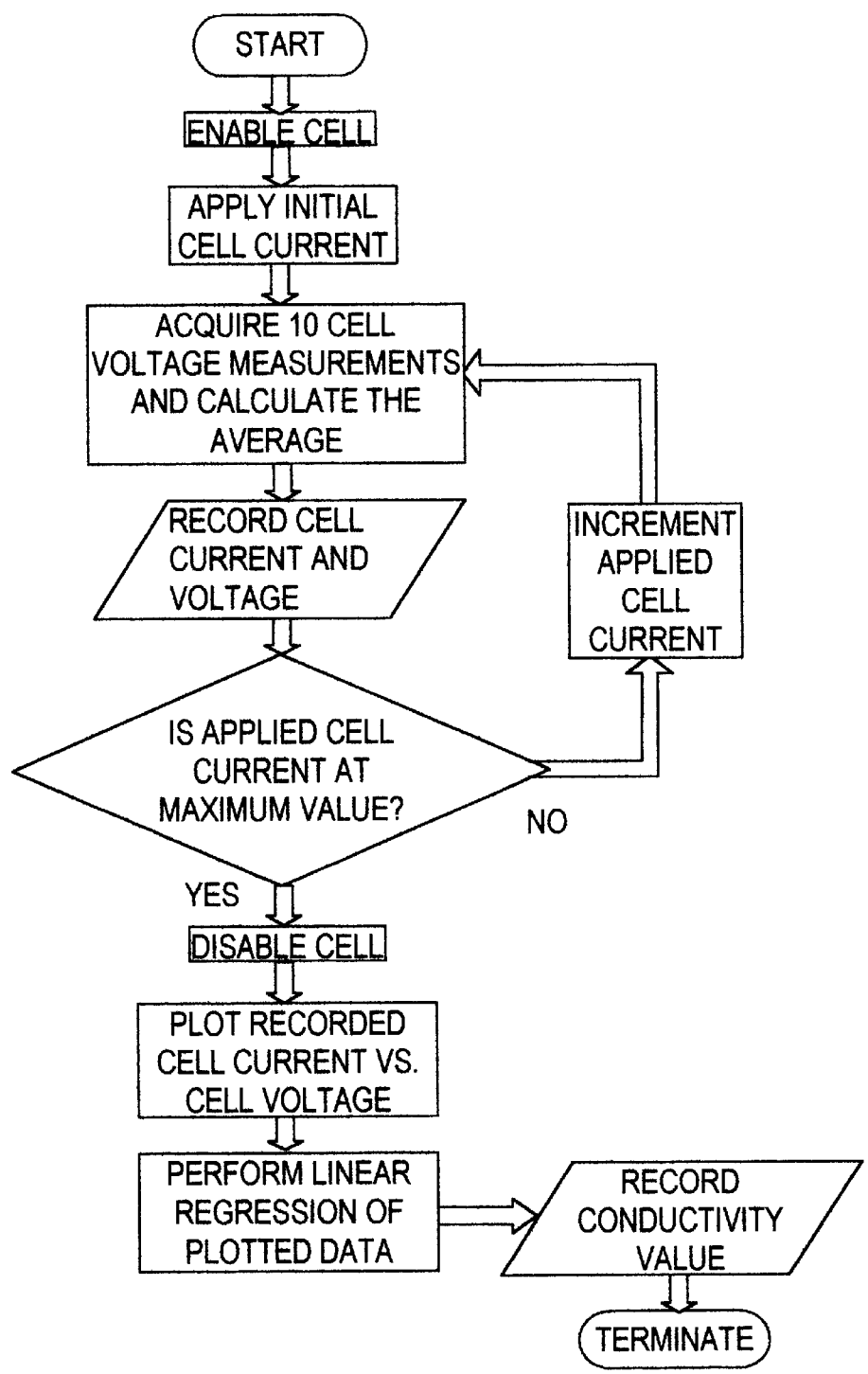
FIG. 10 is a flow chart of an example galvanostat algorithm for use with the disclosed monitoring instrument

FIG. 2 shows the schematics for examples of the three circuits required corrosion monitoring within the instrument 40. FIG. 2a shows the circuitry for a galvanostat 48, which when coupled with an instrumentation amplifier enables conductivity measurements to be made. The algorithm illustrated in FIG. 10 is illustrative of the preferred algorithm for use monitoring the galvanostat 48, although alternative programs can be written that perform the same functions and will be evident to those skilled in the art. Once data is collected for each of the sensors, the data can be compared, plotted or otherwise manipulated and report based on any preprogrammed time period.

Figure 9:
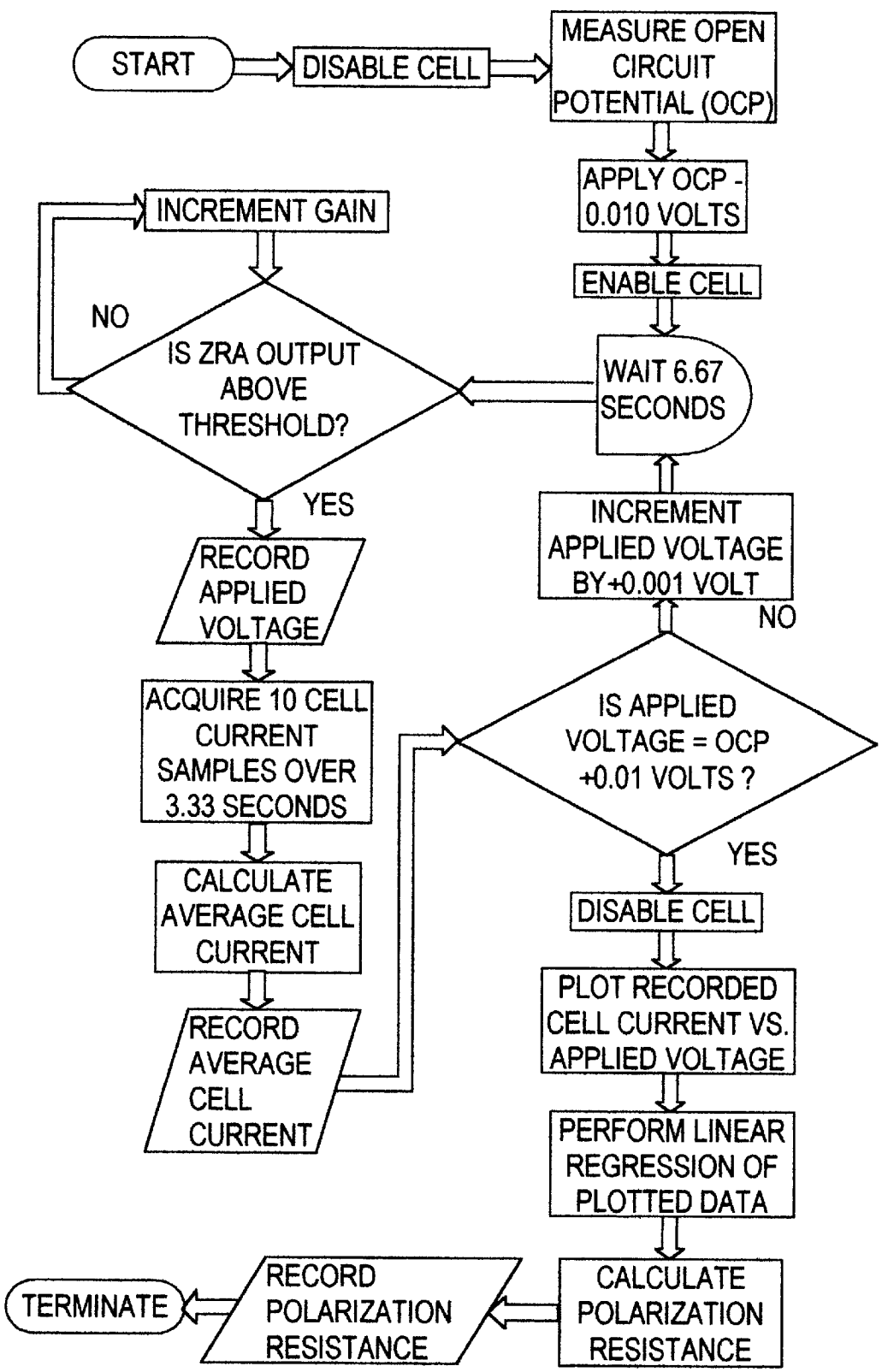
FIG. 9 is a flow chart of an example polarization resistance algorithm for use with the disclosed invention.

FIG. 2b shows a potentiostat 50 and a zero resistance ammeter (ZRA) 152 used to measure polarization resistance that is instrumental in determining corrosion rate. An auto-ranging ZRA is used in the electronic circuitry and software design of this instrument. Prior art devices use a single range zero impedance ammeter circuit in the polarization resistance measurement section of the instrument, significantly reducing the measurement accuracy and range of the device. The use of the auto-ranging ZRA in the instrument 40 enables polarization resistance measurements in a wide range from 1 Kilo Ohm*Cenitmeter$^2$ to 1 Meg Ohm*Centimeter$^2$. The auto-ranging ZRA further enables significantly higher measurement accuracy. Both of these improvements can be attributed to the inclusion of an auto-ranging ZRA used to perform current measurements over five measurement ranges. The auto-ranging function of the instrument's circuitry and software assures that the current flowing between the counter and working electrodes is measured using a range selection, which will yield the highest accuracy. The algorithm of FIG. 9 is designed to run the potentiostat 50, although as stated heretofore, alternate algorithms can be written for use within the system.

FIG. 2c shows a chloride sensor 160 composed of an instrumentation amplifier connected to the Ag/AgCl electrode 56 and the MnO2 electrode 52. Dummy cells (passive R and C elements) will be included in the design of the instrument allowing it to be tested while disconnected from the sensing elements.

Signal Conversion

After electrochemical signals are collected and conditioned by the instrument's front-end analog electronics 10, they must be converted to the digital domain before they can be further processed by the system's microcontroller. This conversion process is achieved using an analog to digital converter (ADC) 20. In addition, excitation potentials must be produced to drive the instrument's electrodes. These excitation voltages are first established as digital information by the system's microcontroller 14, and are then converted to analog signals the digital to analog converter (DAC) 12. ADC and DAC devices are selected for the system based upon sufficient resolution to yield the required accuracy for measurements of $E_{corr}$, $I_{corr}$, conductivity and [Cl$^-$]. These components are also selected to minimize the instrument's power requirement.

System Microcontroller and Related Software

A RISC (reduced instruction set computer) type microcontroller 14 is used as the system controller for the corrosion measuring instrument. RISC type architecture devices are excellent for low power embedded applications. The microcontroller 14 can be placed in an "ultra-low-power" sleep mode for long periods of time between corrosion measurement or data collection cycles. The microcontroller 14 directly controls the system's ADC 20, DAC 12 analog multiplexers in the front-end electronics 10, power management 16 and communications sensors. All of the system's calibration coefficients and other non-volatile data will be stored in the microcontroller's on-board EEPROM.

Each unit contains a programmable gain amplifier and an adjustable low pass filter to permit preprogrammed, or manual, adjustment. The ability to change the gain and filter settings of the system is critical to eliminate electronic noise and change in ambient conditions. Automatic adjustment is advantageous in that it allows the instrument to alter it settings based upon preprogrammed base lines. In this way, the optimal signals for each individual sensor are always transmitted without the need for human intervention.

The software for the instrument can be of any standard or custom programming language, such as C++, Java, etc. Although the basic software driving the peripherals, such as the converters, analog front-end electronics, etc., is similar, each specific application can be custom programmed to meet the end use.

Power Management

The power management system 16 of the hardwired corrosion monitoring instrument 40, and 116 of the wireless monitoring instrument 104, is partitioned into multiple sub-systems, enabling each sub-system to activate a corresponding electronic sensor only when necessary. Each electronic sensor performs a defined action, such as receiving data, sending data, conducting measurements, etc. This technique conserves power by leaving most system components powered down when they are not needed to perform a particular function. Those system components that cannot be completely powered down are placed in a low power "sleep" mode. In most embodiments, the real time clock is the single element unable to be powered down, however depending upon the specific application other sub-systems can require low power "sleep" mode rather than actual power down. Each of the power sub-systems will be activated or de-activated by the system microcontroller. For example, it is necessary to power the optional RF communications sensor 118 only when the data collection system is communicating with the instrument.

The RTC 18 keeps track of the current century, year, month, day, hour and second. This enables the instrument to be programmed, via its LAN connection, to conduct one or more measurement cycles at predetermined times. Once completed, the results of these measurement cycles can be annotated with the current time.

There are significant benefits of having both timekeeping and data-logging functions on the same instrument. For example, the results of pre-programmed measurement cycles can be logged in the instrument's on-board database and retrieved at a later time. This eliminates the need for an operator to be present to initiate a measurement cycle or collect the resulting data.

Data Communications

Once the corrosion measuring instrument 40 has collected corrosion related data, it can be interrogated by a PC or laptop computer or other data logging system for the information that it has collected. If multiple data measurement and collection cycles have occurred between data interrogations, data will be time and date stamped, and stored in the microcontroller's non-volatile volatile EEPROM memory. Upon completion of, or simultaneous with, the interrogation, all stored measurement data is downloaded to the PC or laptop. The instrument is capable of either hardwired or wireless communications. The decision between installing a hardwired or wireless system is dependent upon the final application, location, costs involved, etc. The wireless system 104 is advantageous in that there are no wires to string during installation or wires to break, making installation easier and faster. The hardwired system 40 provides the advantages of low cost, a centralized power source and rapid data collection, however the initial installation process is increased.

In the hardwired system a small multi-conductor cable 60 is attached to the lead instrument 140 and extends out through the concrete under evaluation, connecting to a PC, laptop computer or data logger for data interrogation. An alternate network configuration has each instrument directly connected to the data collection system in a "star" configuration. In this configuration the data collection system serves as the hub of the network. Optionally, a small RF transceiver sensor is mated with the instrument's main printed circuit board allowing the instrument to establish wireless data communications with the interrogating computer. In wireless mode, the serial port of the interrogating PC or laptop computer will also be connected to an RF transceiver. Also, in wireless mode, the instrument can be awakened from low power sleep mode by detecting the presence of an externally generated RF signal.

The software can be set to provide minimal data, which will allow the user to issue a limited set of basic commands to the instrument and receive data from the instrument in a textual format with the PC running a terminal emulator program. Alternatively, the software can interact with a windows based application being run on the PC that incorporates specific graphical user interface (GUI) capable of additional processing of the data that it has received and displays the data in a graphical format.

As these are embeddable systems, the instrument cases 570 and 600, as illustrated in FIGS. 11–18, must be capable of supporting large amounts of weight without cracking and permitting chemicals to contact the electronics. In order enable the instrument cases 570 and 600, as disclosed herein, to withstand the level of pressure that would be applied by tons of concrete, the design and construction materials are critical.

The material used must have a chemical resistance to any chemicals that would be contained in the support material. For example, in concrete the instrument cases 570 and/or 600 must have the ability to resist degradation from salts, such as sodium or calcium chloride, as well as other chemicals having an alkalinity as high as pH13. To prevent cracks from forming, the instrument 500 material needs the ability to flex and have a failing point at least equal to the material within which it is embedded. To ensure resistance to failure the instrument material preferably has a stiffness and flexural modulus to match the stiffness and flexural modulus of its environment. An example of an appropriate material for many environments is Valox, EF4530 which is a 30% glass reinforced plastic having a 1.675 mega psi flexural modulus. Other materials, having specific properties to withstand the surrounding environment, will be evident to those skilled in the art. To obtain optimum results, the flexural modulus of the material of manufacture for the instrument case should follow the formula of:

$$\frac{Stress}{Strain} \text{flexural modulus}$$

In accordance with the above formula, concrete having a 3 milli strain failure point would exert about 4,000 pounds of stress on the instrument case. Therefore, the material used for the case 500 must have a flexural modulus of at least 1.33 MPSI to have sufficient strength to withstand that level of stress.

To further reduce the chances of cracking and breakage, the construction of the instrument cases 570 and 600, as disclosed, are designed with curved corners. The curved corners serve to eliminate high stress points on the enclosure where cracking can occur.

The face 502 of the cover 504 for use with either the instrument cases 570 or 600, or other case, without the electrodes inserted is illustrated in FIG. 11. In the preferred embodiment the cover 504 has protective trays 540 and 560 that extend from the face 502 at about a 90° angle and form a wall on all sides around the electrodes. The protective trays 540 and 560 serve to protect any wire electrodes, such as the chemical electrodes illustrated herein, from damage during installation and encasement within the structure, in addition to any shifting of the structural material. The height of the tray edges 546 and 566 of the protective trays 540 and 560 must be sufficient to extend slightly above the tray surface 542 and 562 equal to the depth of the electrodes maintained therein. As illustrated, the protective trays 540 and 560 preferably have rounded edges, again to facilitate the flow of stress around the extensions. The side views of FIGS. 12 and 13 further illustrate how the protective trays 540 and 560 extend above, and are preferably integral with, the face 502. FIGS. 12–14 also illustrate the electrode channels 564 and 544 that bring the electrode wires through the solid cover 504 for exposure to the surrounding structure material. As disclosed herein, to obtain optimum readings, all electrodes should extend equal distance from the face 502. The protective trays 540 and 560 enable the wire electrodes to extend a distance from the face 502 equal to that the more rugged reference and working electrodes 52 and 42, without bending or distorting. In order to achieve this, the tray surface 542 and 562 is raised from the face 502 an amount slightly less than the height, or protrusion, of the rugged reference and working electrodes 52 and 42. The height of the tray surface 542 and 562 is determined by the height of the rugged electrodes less the height of the wire electrodes and amount of protrusion required to enable the electrode to operate. If, however, only wire electrodes are being used they can be embedded directly within the cover face and protected in the same way as disclosed herein. The protective trays 540 and 560 as illustrated herein, are dimensioned to surround the electrodes illustrated herein and be of any dimensioning or configuration necessary to protect the electrodes being used with the specific instrument.

The rugged reference and working electrodes 52 and 42 are, in the embodiment illustrated herein, received in ports 510 and 508. The reference and working electrodes 52 and 42 are brought through the cover 504 at channels 534 and 532. As these electrodes are heavier and more durable, they can be placed into direct exposure with the surrounding material without the need for protective trays.

In order to provide protection for the counter electrode 44, which extends through channel 536 and exits at port 530, the mesh or plate counter electrode receiving area 512 is slightly recessed by a distance equal to, or slightly greater than, the thickness of the mesh or plate. The counter electrode 44 in this embodiment is secured to the electrode receiving area 512 at multiple plastic weld spots 506, however other means to secure the electrode can also be used as long as surrounding environmental considerations are met. As stated heretofore, the larger, more rugged electrodes such as the MnO2 reference electrode 52 and the working electrode 42 have sufficient strength to stand on their own without the need for the reinforcement provided by the protective trays 540 and 560. It should be noted that in most applications the monitoring instrument is installed with the face 502 facing the diffusion front of corrosive elements. For example in a bridge, the electrodes would extend toward the surface of the bridge while in marine applications, the electrodes would extend toward the surface of the submerged portion of the structure.

Figure 15:
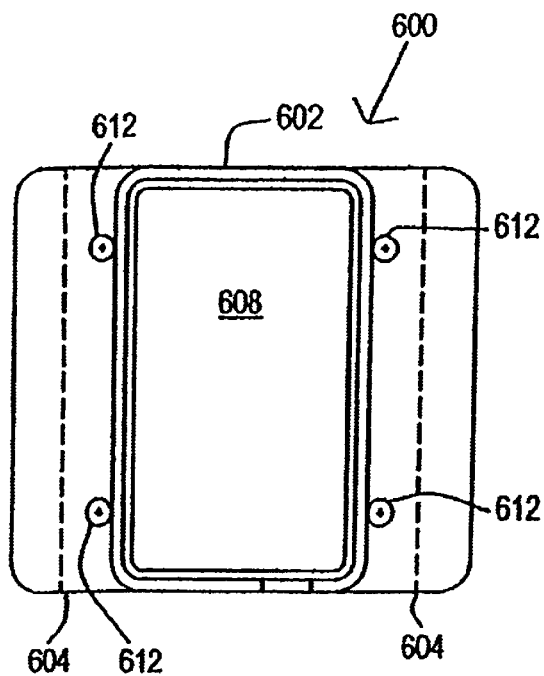
FIG. 15 is a top view of the instrument case illustrating the preferred attachment method.
Figure 16:
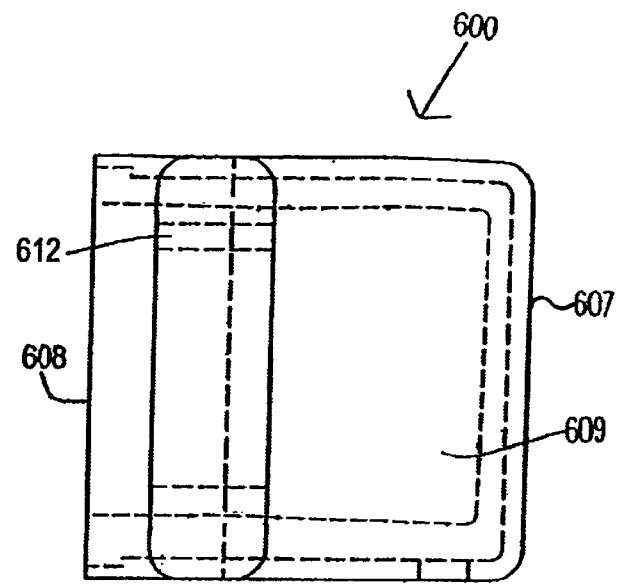
FIG. 16 is a long side view of the embodiment of FIG. 15.
Figure 17:
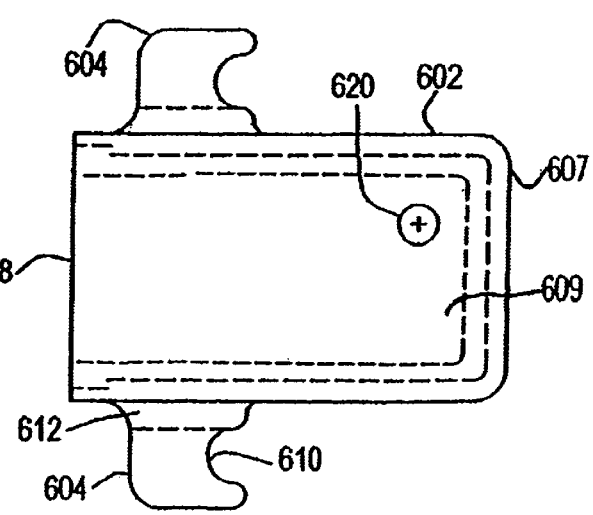
FIG. 17 is an narrow side view of the embodiment of FIG. 15.

In FIGS. 15–17 the preferred method of securing the case 600 to the rebar is illustrated. In this embodiment, the case body 602 has two arced wings 604 extending along the long side 606 of the body 602. This configuration enables the case 600 to be oriented with the electrodes facing the diffusing material changes. The cover receiving side 608 is dimensioned to receive the cover 504, which once all of the electrodes and monitoring electronics 609 are positioned within the case 600, protected by the closed end 607, is secured to the body 602 with a waterproof adhesive. Preferably the arc interior 610 has a circumference about equal to, or slightly greater than, that of the rebar or other structural support materials to which it is being attached. For example, when used in concrete reinforced structures, four fourteen inch or longer pieces of rebar, generally in the range of about #3 rebar, are formed into a polygon supplemental support structure to maintain the instruments in place. These supplemental support structures are then rigidly attached to the surrounding structural reinforcement members. This use of a polygon supplement support structure not only provides support for the instrument but prevents, or reduces, cracking of the surrounding concrete. Channels 612 enable ties, wire or other attachment methods to be used to secure the case 600 to either the main support structure or the supplemental support structure. Although the cable port 620 is illustrated in one of the narrow sides of the case 600 (in this and other embodiments), the cable port 620 can be located at any location convenient for manufacture.

Figure 18:
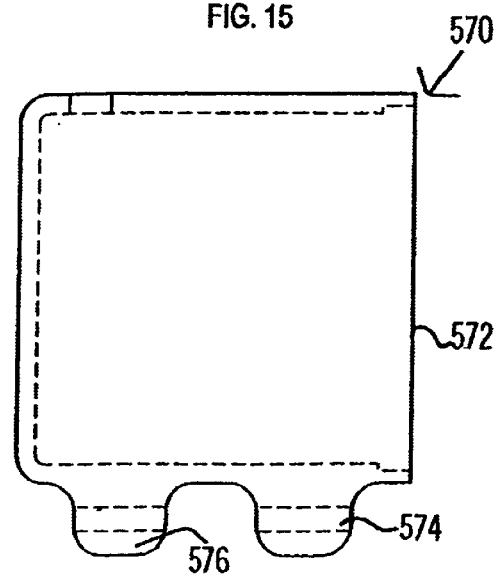
FIG. 18 is a side view of the instrument case illustrating an alternate attachment method.

An alternate electrode retaining case 570 is illustrated in FIG. 18 wherein mounting flanges 576 replace the arced wings 604 to enable the case to be mounted adjacent the rebar. The mounting flanges 576 contain channels 574 which are provided to receive a tie, wire or other securing device. As can be seen from this illustration, the corners of the electrode retaining case 570 are curved to direct the flow of stress lines.

This method of mounting also provides a protective reinforcement cage surrounding the instrument. This additional reinforcement helps to prevent crushing and cracking of the material in the near vicinity of the instrument.

It should be noted that when referred to herein the term electrodes applied to any sensor, gauge or other sensing device that take a reading from the surrounding materials.

An example of specifications for a hardwired, corrosion monitoring instrument for steel reinforced concrete would be:

Physical Dimensions
  Enclosure—85 mm (L)×80 mm (W)×50 mm (H)
  Enclosure and Electrodes—122 mm (L)×80 mm (W)×50 mm (H)
Enclosure Material
  ABS Plastic
  Water Tight Seal
Chloride Measurement
  Range—0.01%→≧1% Chloride
  Electrodes (2)—Ag/AgCl (1) 14.5 mm (L)×1 mm (D), $MnO_2$ (1) 13.5 mm (D)×8 mm (H) (concrete)
Conductivity/Resistivity Measurement
  Range—15,000→1,000 Ohm-cm
  Electrodes (4)—Au or Stainless Steel (4) 12 mm (L)×0.5 mm (D) spaced at 12 mm
Polarization Resistance Measurement
  Range—1 MOhm-$cm^2$→1 KOhm-$cm^2$
  Electrodes (3)—Pt/Nb mesh or Stainless Steel plate or mesh counter electrode (1) 18 $cm^2$×1 mm thick, $MnO_2$ reference electrode (1) 13.5 mm (D)×8 mm (H) (concrete) shared with Chloride measurement, Steel working electrode (1) 12.5 mm (D)×22 mm (H)
Temperature Sensor
  Range—−55° C. to +150° C.
Estimated Power Requirements
  Strain Gauge Inactive—1.5 mAmps @ 3.3 Volts<5 mWatts
  Strain Gauge (120Ω) Active—29 mAmps @ 3.3 Volts<100 mWatts
Communications
  Protocols
    SDI-12 Protocol
    HART Protocol
    CAN Protocol
    LON Works Protocol
  Network
    RS-232
    RS-485
    RS-422
    LVDS
    TTL
    CMOS
    4–20 mA Current Loop
  Wireless
    Terrestrial Cellular
    RF
    Satellite
Strain/Strain Measurement
  Strain Gauge—supports 1 to 4 element gauges
  Internal Excitation Source
Power Supply
  Rechargeable battery (external to the bridge) charged by Solar Collector
Embedded Self-Powering Source
  Energy storage device—Rechargeable battery or a "Super Capacitor" charged by
    Rectification of RF energy
    Electrochemical potential via galvanic couples
    Piezoelectric generation and rectification
Vibration and Acceleration Measurements
  Onboard Piezoelectric Accelerometer It should be noted that although the above is described as an individual system with a single local readout, it should be noted that the system can be networked with the data being transmitted from the local computer to a centralized system, via satellite or hardwire network, where it is fed into a system provider. This would enable a government agency or private provider, to monitor multiple structures from a single location.

What is claimed is:

1. A system for monitoring the material changes in a structure using:
  at least one monitoring instrument, each of said at least one monitoring instrument having a body, an individual ID and being embedded within said structure and having:
    at least one electronic module, each of said at least one electronic module having sensors in contact with said material and electronic monitoring means within said monitoring instrument to receive signals from said sensor;
    an analog to digital converter, said analog to digital converter receiving analog signals from each of said at least one electronic monitoring means;
    a microcontroller, said microcontroller receiving signals from said analog to digital converter;
    a digital to analog converter, said digital to analog converter converting signals from said microcontroller to each of said at least one electronic monitoring means; and
    transmission means, said transmission means to transmit said digital signals to a data logger;
  power means, said power means providing power to each of said at least one electronic module;
  potting material, said potting material encompassing said modules within said monitoring instrument;
  a data logger, said data logger being external from said structure and receiving and storing said digital signals;
  wherein said monitoring instrument receives signals from said at least one electronic module, converts said signals from analog to digital and transmits said digital signals for each of said at least one monitoring based on said ID to said data logger.

2. The system of claim 1 wherein said data logger displays said digital signals.

3. The system of claim 2 wherein said data logger is a computer.

4. The system of claim 1 wherein said analog to digital converter amplifies and filters said signals, said amplification and filtration being programmable from said data logger.

5. The system of claim 1 further comprising a power management system, said power management system being in communication with each of said at least one electronic module, said analog to digital converter, said microcontroller, and said digital to analog converter, said power management system regulating power consumption by placing each of said at least one electronic module, said analog to digital converter, said microcontroller, and said digital to analog converter in a sleep mode when not in use.

6. The system of claim 1 wherein said material change is corrosion.

7. The system of claim 6 wherein one of said at least one electronic module measures conductivity.

8. The system of claim 6 wherein one of said at least one electronic module measures linear polarization resistance.

9. The system of claim 8 wherein said at least one electronic module has a steel working sensor and a stainless steel reference sensor to measure linear polarization, said steel working electrode having an exterior surface matching an exterior surface of structural reinforcement steel surrounding said monitoring instrument.

10. The system of claim 6 wherein one of said at least one electronic module is capable of measuring chloride concentration.

11. The system of claim 10 wherein said at least one electronic module has a Ag/AgCl chloride ion specific sensor and a MnO2 reference sensor, said voltage potential between said ion specific sensor and said MnO2 reference sensor indicating said chloride concentration.

12. The system of claim 1 wherein each of said at least one monitoring instrument is networked to, and communicates with, at least one other of said at least one monitoring instrument.

13. The system of claim 1 wherein said power means are external to said structure, said power means being hardwired to each of said at least one monitoring device.

14. The system of claim 1 wherein said monitoring device further comprises at least one local power means, said local power means generating power for each of said at least one electronic module.

15. The system of claim 14 wherein said local power means is at least one from the group comprising a piezoelectric generator; an electrochemical galvanic couple; and/or a RF power receiver using an impedance matching network.

16. The system of claim 1 wherein a first end of each of said sensors is on a first plane, thereby enabling said material changes to come in contact with each of said sensors about simultaneously.

17. The system of claim 1 wherein communication between said data logger receives said each of said at least one monitoring instrument is wireless.

18. The system of claim 17 wherein said wireless communication is RFID.

19. The system of claim 1 wherein said monitoring instrument is hardwired to said data logger.

20. The system of claim 1 wherein one of said at least one electronic module is a temperature module, said temperature module having temperature recording and transmitting means.

21. The method of monitoring corrosion in a steel reinforced concrete structure comprising the steps of:

assembling a monitoring device having electronic sensors having electrodes;

positioning said electronic sensors within a protective case to enable said electrodes to contact said concrete;

securing said electronic sensor within said protective case with a potting material;

placing at least one monitoring device within said concrete during construction, said monitoring device containing electronic sensors having electrodes to monitor said corrosion;

assigning each of said at least one monitoring device an ID number;

networking each of said at least one monitoring device with other of said at least one monitoring device;

connecting one of said at least one monitoring device to a data logger;

completing said concrete structure;

monitoring signals sent from said electronic sensors indicating corrosion levels within said structure at said data logger.

22. An instrument case to enable electronic sensors to be embedded into a structural material, said instrument case having:

a hollow body, said hollow body being manufactured from a material having a flexural modulus at least equal to said structural material stress divided to by said structural material strain and having a first end, a closed second end and multiple sides each of said multiple sides having a connection length with an adjacent side, said body being configured to contain and protect electronic modules from contact by said structural material;

at least one electrode receiving port in said first end, each of said at least one electrode receiving port enabling an electrode to contact said structural material;

at least one protective tray, each of said at least one protective tray extending from said first end at about a right angled to surround said at least one electrode receiving port;

at least one electronic sensor, said at least one electronic sensor being within said hollow body to receive data from said electrodes and transmit said data to a data gathering source;

at least one cable port to receive a network cable;

wherein said adjacent connection lengths are rounded to direct pressure from said structural material around said instrument case thereby preventing said instrument case from developing cracks from said pressure.

23. The instrument case of claim 22 further comprising attachment flanges, said attachment flanges being integral with said hollow body and tie receiving channels, thereby enabling said instrument case to be attached to reinforcement members within said structural material.

24. The instrument case of claim 22 further comprising at least one electrical sensor, each of said at least one electrical sensor having at least one external electrode and an internal electronic monitor means, said electronic monitoring means being within said instrument case and each of said at least one electrodes extending through said at least one electrode receiving port to place a first end of each of said at least one electrode in contact with said structural material and a second end of said electrode in electronic contact with said electronic monitoring means.

* * * * *